United States Patent [19]

Sandegren

[11] 4,131,217
[45] Dec. 26, 1978

[54] DEVICE FOR EMPTYING A CONTAINER

[75] Inventor: Owe Sandegren, Skärhamn, Sweden

[73] Assignee: Landstingens Inkopscentral, L I C, Svetsarvagen, Sweden

[21] Appl. No.: 798,291

[22] Filed: May 19, 1977

[51] Int. Cl.² .............................................. B67B 7/28
[52] U.S. Cl. ..................... 222/82; 222/83.5; 222/103; 222/214; 222/326; 128/216; 128/232
[58] Field of Search ................... 222/82, 83.5, 88, 95, 222/103, 105, 214, 326, 327, 386.5; 128/216, 232, 231

[56] References Cited

U.S. PATENT DOCUMENTS

| 425,221 | 4/1890 | Harden | 222/105 |
| 798,093 | 8/1905 | Dean | 222/95 X |
| 2,471,852 | 5/1949 | Bau | 222/95 |
| 2,688,964 | 9/1954 | Smith | 128/216 |
| 2,771,879 | 11/1956 | Salisbury, Jr. | 128/216 |

FOREIGN PATENT DOCUMENTS

| 823413 | 10/1937 | France | 222/95 |
| 114199 | 3/1926 | Switzerland | 128/216 |

Primary Examiner—Robert B. Reeves
Assistant Examiner—Charles A. Marmor

[57] ABSTRACT

A device for emptying a container of the type comprising two domed parts of different stiffnesses sealed along a joint and having an outwardly directed flange adjacent the joint. A holder for the container has an opening and a member defining a gap to position and receive most of the container flange. The opening and the gap defining member are so arranged that when the flange is inserted in the gap, the outlet of the container is located substantially in line with the holder opening. An emptying member is provided opposite the holder opening and is manually displaceable in the direction thereof for emptying the container. In one embodiment, the holder is the cylinder of a piston and cylinder arrangement, the piston of which forms the emptying member while in another embodiment, the holder is in the form of an annular structure, one part of the wall of which has enhanced flexibility so as to form the emptying member.

3 Claims, 2 Drawing Figures

DEVICE FOR EMPTYING A CONTAINER

The present invention relates to a device for emptying a container, the container being of the type comprising two substantially dome-shaped container parts, the concave surfaces of which face each other, the parts communicating with each other to form a container sealed along a joint between the parts and having an outwardly directed flange adjacent the joint, one of the container parts being relatively stiff in comparison with the other and being provided with means defining an outlet opening and the other part being more flexible to enable it to be pressed into the stiff container part and substantially into alignment with the inside thereof in order to empty the container. Such a container may contain liquid, such as liquid to be injected, cream, powder or the like.

Earlier proposals for emptying a container of the type mentioned lack any special aids, the idea being to use the flange protruding from the joint between the two dome-shaped container parts as a sort of finger support. However, it has been found in practice that in most cases such an emptying procedure did not have the requisite stability. The container may easily slip from the hand and dosing is difficult to effect.

As early as 1910 (see United States Patent Serial Number 978,488) it was proposed to empty conventional ampoules by means of an injection syringe. However, the ampoule became crushed in a quite uncontrolled manner and it was generally impossible to fully empty the contents out, thus making it extremely difficult to perform accurate dosing. Furthermore, a conventional syringe is complicated and expensive.

According to the present invention, there is provided a device for emptying a container of the type comprising two substantially dome-shaped container parts the concave surfaces of which face each other, the parts communicating with each other to form a container sealed along a joint between the parts and having an outwardly directed flange adjacent the joint, one of the container parts being relatively stiff in comparison with the other and being provided with means defining an outlet opening and the other part being more flexible to enable it to be pressed into the stiff container part and substantially into alignment with the inside thereof in order to empty the container, the device comprising a holder for such container said holder having an opening and means defining a gap to position and receive most of the flange of such container, the opening and the gap-defining means being arranged in relation to each other so that when the flange, in use, is inserted in the gap, the container outlet opening is located substantially in line with the opening of the holder; a member located opposite the holder opening and manually displaceable, in use, in the direction thereof, for emptying the container, upon displacement of the member a distance in the direction of the opening sufficient as to press in the flexible container part to substantially abut the inside of the stiff container part secured in the holder.

In a preferred embodiment the front end of the emptying member in the direction of movement is rounded, having substantially the same dome-shape as the inner side of the stiff container part. Upon direct contact with the flexible container part, therefore, the rounded end of the emptying member will bring this substantially into abutment with the inside of the stiff container part so that the container can be deformed in a controlled manner upon emptying and complete emptying is facilitated. To make this embodiment as inexpensive as possible without ignoring the other requirements, it is suitable for the emptying member and the holder to be made in one piece and joined together by means of sections having sufficient flexibility as to permit displacement of the emptying member.

Embodiments of the present invention can also be used as injection syringes if the containers are in the form of ampoules, containing an injection solution and having an outlet opening provided with a membrane. In such a case the opening of the holder may suitably be arranged to take a cannula, the rear end of the cannula when in the operative position being located immediately opposite the membrane located in the outlet opening of the ampoule so that the membrane is arranged to be punctured by the rear end of the cannula when the ampoule is emptied.

When precise positioning is required, it is desirable for the holder to comprise a cylinder and a sleeve surrounding one end of the cylinder and detachably attached thereto, the sleeve having an inwardly protruding flange member which, in the longitudinal direction of the cylinder limits the gap between itself and the neighbouring end surface of the cylinder in order to position the flange member of the container, and for the device to comprise a piston displaceable in the bore of the cylinder. The advantage of easy insertion and receipt of the container is therefore obtained and the attachment of the sleeve on the cylinder can easily be designed so that the flange of the container is clamped axially in the gap. Furthermore, a first sealing ring may be arranged to seal between said end surface of the cylinder and the flange of the container and a second sealing ring may be arranged to seal between the bore of the cylinder and the displaceable piston. The first sealing ring contributes to the firm positioning of the container, and together the sealing rings serve to seal a space defined by the cylinder bore, the piston and the flexible container part. The air column enclosed in this space serves to transmit movement and is able to transmit the axial movement of the piston to the flexible container part without the necessity of direct contact between them and this irrespective of the direction of movement of the piston.

In the following the invention will be further described with reference to the accompanying drawings. Although the embodiments in the drawings refer to a specific application of the invention, namely as emptying means for injection solutions, the invention is of course not limited to such embodiments. In the drawings.

Figure 1:
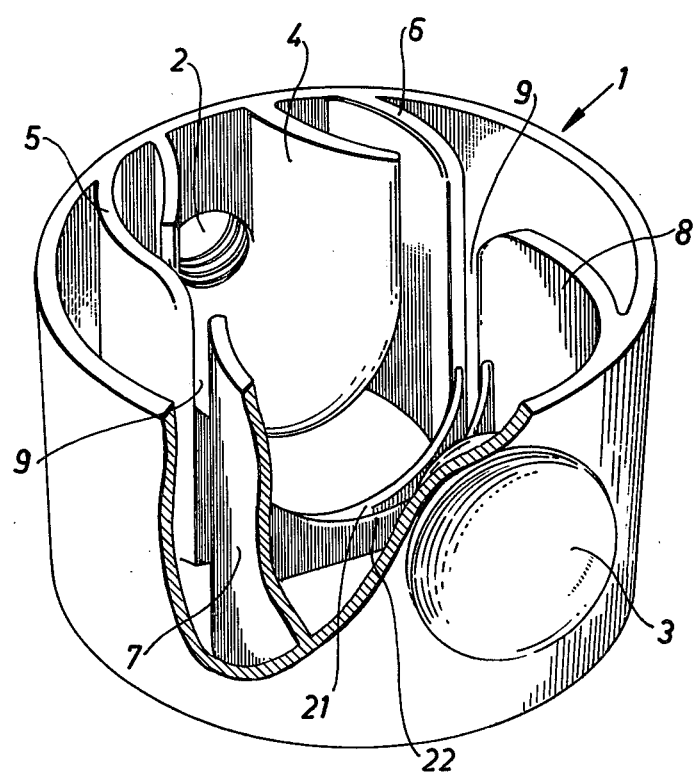
FIG. 1 is a partially broken perspective view of a first embodiment of the invention.

In FIG. 1 the emptying device is designated generally 1. The device has substantially annular structure and comprises an outer casing provided with a front opening 2 and located diametrically opposite to the opening, a rear, inwardly directed dome 3 protruding from the inside of the casing in the direction of the opening 2. To facilitate the description, it is assumed that the end surfaces of the casing are horizontal. The opening 2 is surrounded below and at the sides by a support wall 4, substantially U-shaped in vertical cross-section, protruding from the inside of the casing and flaring like a funnel towards the central axis of the emptying means. Substantially vertical guide walls 5 and 6 protrude from the wall to each side of the opening 2 are spaced from the wall 4 and extend towards a transverse, vertical, central plane through the central axis of the device. Substantially vertical guiding walls 7 and 8 similarly protrude towards the vertical, central plane from portions of the opposite side of the casing wall to each side of the dome 3. The guide walls 5 - 8 are slightly curved longitudinally of the device and the free ends of the walls 5 and 6, 7 and 8 are joined at the bottom by means of straight transverse walls 21 and 22, respectively, the upper edges of which are curved in longitudinally of the device so that the transverse walls are lowest in the middle. Between the end surfaces of the guiding walls 5 and 7, 6 and 8, facing each other and between the side surfaces of the transverse walls 21 and 22 facing each other, therefore, a gap 9 is formed having uniform width and intended to position a container 11, in the following exemplified by an ampoule.

Figure 2:
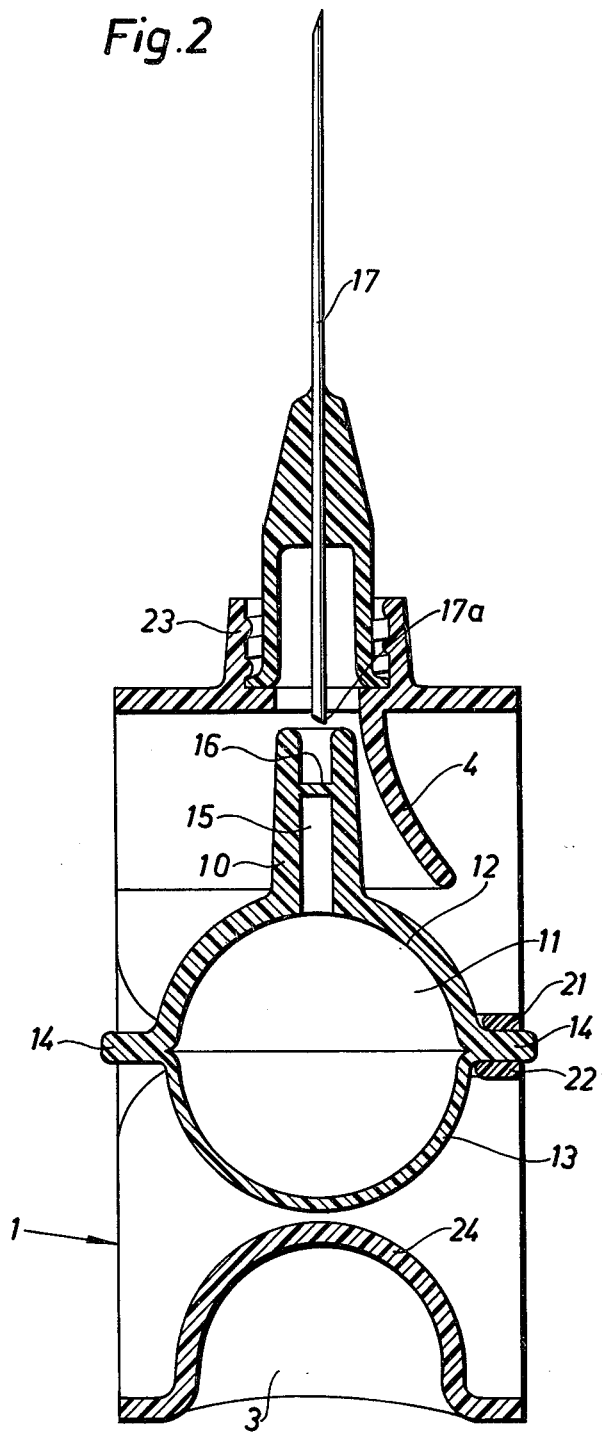
FIG. 2 shows a longitudinal section through the emptying means according to FIG. 1, but with a cannula in position and ampoule inserted.

As can be seen from FIG. 2, the ampoule 11 consists of two substantially dome-shaped parts 12 and 13, the open ends of which face each other and are sealed together to form an ampoule with a flange formation 14 protruding substantially radially from the line of connection of parts 12 and 13.

When the ampoule 11 is inserted in the device 1, the flange formation 14 is received in and positioned in the gap 9 and the ampoule is inserted until it abuts the transverse walls 21 and 22, the upper edges of which are shaped to conform with the outer surface of the ampoule 11. The gap 9 receives more than half of the flange formation 14 extending around the ampoule 11.

One part 12 of the ampoule is relatively stiff and is provided with means 10 defining an outlet opening 15. This is shown in the form of a straight nozzle 10 extending radially from the ampoule substantially perpendicularly to the plane of the flange formation 14. The other part 13 of the ampoule is flexible to enable it to be pressed into the stiff part 12 of the ampoule and be brought substantially into abutment with the inside thereof in order to empty the ampoule 11 through the outlet opening 15. To avoid contamination of the contents of the ampoule, as well as accidental emptying of some of the contents of the ampoule, the outlet opening 15 is blocked by a membrane 16 located at a point within the nozzle 10 spaced from its outlet end so that it is difficult unintentionally to puncture it. When the ampoule 11 is inserted to its intended position in the emptying means the outlet nozzle 10 is located in line with the opening 2 in the emptying means.

A cannula 17 is shown inserted in the opening 2, screwed into an internally threaded collar 23 projecting radially from the outside of the casing and surrounding the opening 2. The cannula has a freely projecting rear end 17a which, when the cannula is in place, is directed towards the membrane 16 but terminates a short way from the opening of the outlet nozzle 10.

The emptying device 1 is made in one piece out of suitable plastics material, the walls included in the device being of such a thickness that the means is elastomerically deformable in the direction from the dome 3 towards the opening 2. Together with parts of the outer casing, the guiding walls 5–8 and the transverse walls 21 and 22 form a holder for the ampoule. The holder comprises the opening 2 and the members defining the gap 9. These gap-defining members consists, as is clear from the above, of the end surfaces of the guiding walls 5 and 7; 6 and 8 facing each other, and of the side surfaces of the transverse walls 21 and 22 facing each other.

Figure 3:
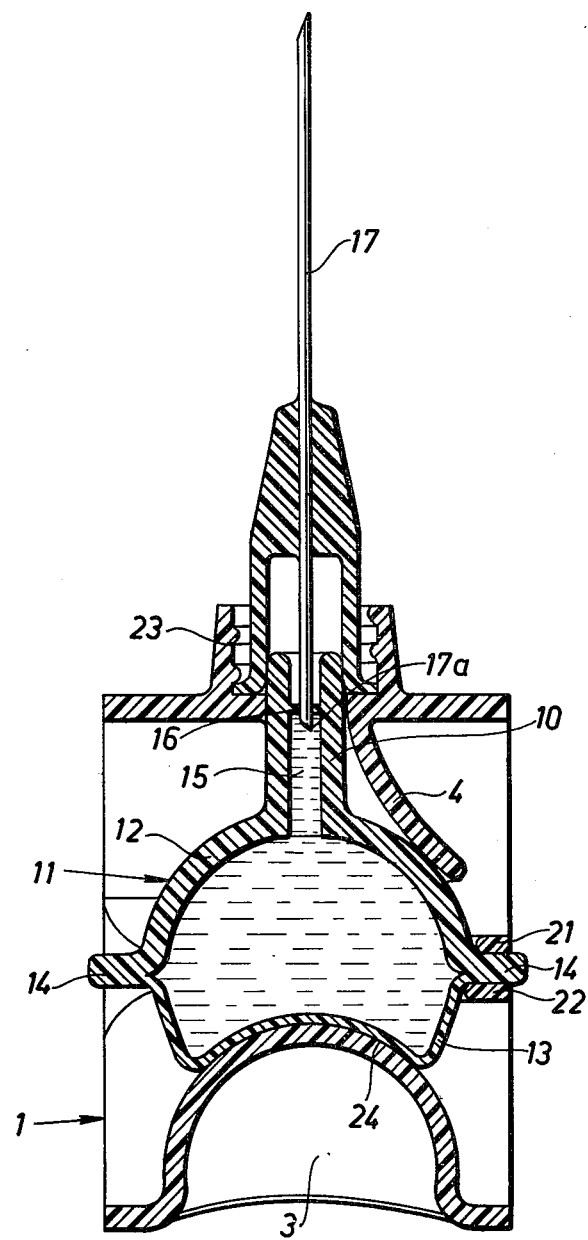
FIG. 3 shows the same section through the means shown in FIG. 2 during emptying of the ampoule.

When the ampoule is inserted, the dome 3 protrudes in towards the flexible rear part 13 of the ampoule 11, terminating a short distance therefrom. The dome 3 thus constitutes a member located opposite the opening 2 which can be manually displaced in the direction of said opening to empty the ampoule upon displacement of the emptying member 3 a sufficient distance in the direction of the opening 2 to press the flexible ampoule part 13 so substantially to abut the inside of the stiff part 12 of the ampoule secured in the holder. The front end 24 of the dome 3 of the emptying device in the direction of movement is rounded, having substantially the same dome-shaped contour as the inside of the stiff part 12 of the ampoule. Usually the material of the flexible part 13 is so thin that its effect can be disregarded. Otherwise, the outer dimensions of the emptying member or dome 3 must of course be correspondingly reduced. Due to this dome-shaped contour the dome or emptying member 3, when brought into direct contact with the flexible part 13, can bring this substantially into abutment with the inside of the stiff part 12. Since the emptying means is elastomerically deformable, the ampoule 11 and cannula 17 will approach each other when the dome or emptying means 3 is pushed in the direction of the opening 2, so that the rear end 17a of the cannula 17 punctures the membrane 16, whereupon the support wall 4 will abut the stiff part 12 of the ampoule 11 and, as can be seen in FIG. 3, prevents the cannula from penetrating through the whole nozzle 10 right into the interior of the ampoule 11 where it might otherwise puncture the flexible part 13. Additional security is obtained if the freely projecting rear end 17a of the cannula is made slightly shorter than the length of the nozzle 10. At the start of an injection process, therefore, the rear end 17a of the cannula punctures the membrane 16. When the injection process is complete the emptying means 1 resumes its original shape and the empty ampoule 11 can easily be removed.

Figure 4:
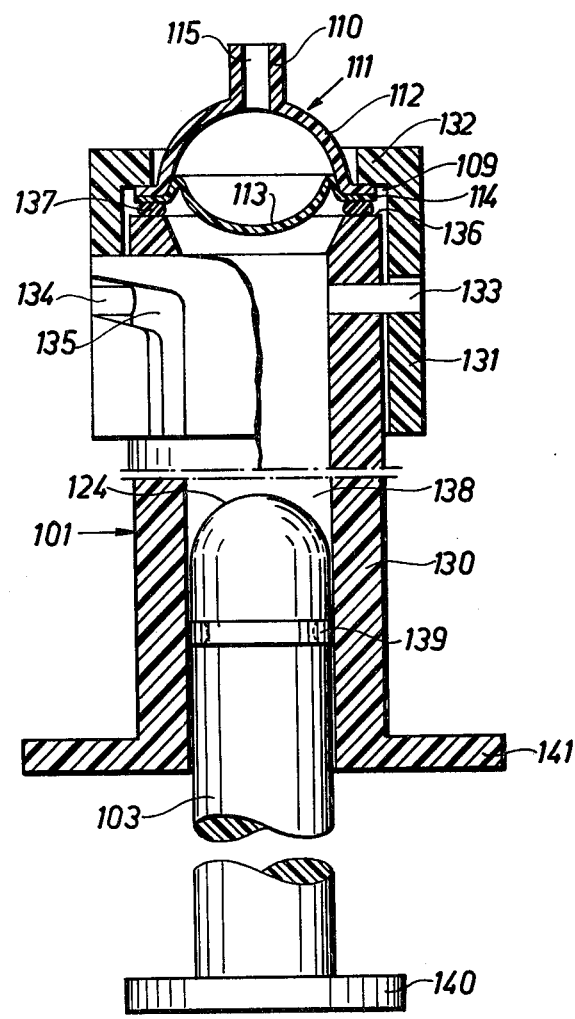
FIG. 4 is a longitudinal section through a second preferred embodiment of the invention.

FIG. 4 shows a container or ampoule 111 which differs from the ampoule 11 described above primarily in that the flexible part 113 is secured to the stiff part 112 not only at the flange 114 but also along a short piece of the dome-shaped inside of the stiff part 112, thus giving the desired protection against leakage. As before, the ampoule 111 comprises an outlet member in the form of a nozzle 110 defining an outlet opening 115 arranged as described above. Of course the nozzle 110 also includes a membrane corresponding to the membrane 16 although this is not shown.

In the embodiment shown in FIG. 4 the emptying device 101 comprises as before a holder for the ampoule 111 and a manually displaceable emptying member 103. The holder comprises a cylinder 130 and a sleeve 131 surrounding one end of the cylinder and detachably attached thereto, said sleeve having an inwardly directed flange member 132. The easily detachable attachment is shown as achieved by means of a bayonet coupling. As is known, this consists of two pins 133 and 134 protruding radially from the cylinder 130 and diametrically opposite to each other, and for each pin is provided a respective groove 135 in the sleeve 131, only one of which is shown. The groove 135 which in the embodiment shown extends radially through the material of the sleeve 131 from its inside to its outside has an axial starting section beginning at one end of the sleeve and an end section forming an angle of slightly less than 90° with an imagined extension of the starting section.

In the longitudinal direction of the cylinder 130 the flange member 132 of the sleeve defines a gap 109 between itself and the neighbouring end surface 136 of the cylinder for receipt and positioning of the flange member 114 of the ampoule 111. A first sealing ring 137 is also arranged to seal between the end surface 136 and the flange member 114 of the ampoule.

In this embodiment the emptying member 103 consists of a piston displaceably arranged in the bore 138 of the cylinder 130. As can be seen in FIG. 4, the piston 103 may comprise a piston rod and a second sealing ring 139 may be arranged to seal between the cylinder bore 138 and the piston rod 103. In this case it is advisable for the second sealing ring 139 to be fixed to the piston rod 103 by being located in a peripheral groove arranged therein, whereas the first sealing ring 137 may be secured to the end surface 136 of the cylinder 130 by glueing.

Like the other components making up the emptying device 101, the piston rod 103 may suitably consist of a stiff, transparent plastics material, such as acrylic resin, may be designed with a rounded front end 124 of the same type as the end 24 described above. However, if the sealing rings 137 and 139 are used, this is not generally necessary, but in the absence of such sealing rings it is usually to be preferred rather than having to fulfil stringent requirements of tolerance and surface finish.

As usual it is advisable for the end of the piston rod 103 projecting from the cylinder 130 to be provided with a support plate 140 for the thumb and the corresponding end of the cylinder 130 to be provided with a transverse projection 141 for the index and the middle fingers.

Although the devices described above and shown in the drawings have been termed an emptying device they can, within the scope of the invention, be used to first fill an initially empty container or ampoule and/or give aspiration ability. In the embodiment according to FIG. 4, which includes sealing rings this is a natural development of the construction, but in the absence of sealing rings and in the embodiment according to FIGS. 1 to 3, the emptying member 3 or 103 can be designed, when manually or automatically withdrawn, to take with it the flexible ampoule part 13 or 113 by placing a drop of glue or the like to temporarily join the part 13 or 113 of the ampoule to the rounded end 24 or 124 of the emptying member 3 or 103.

I claim:

1. In combination, a container and a device for emptying the container, the container comprising two substantially dome-shaped container parts, the container parts having respective concave surfaces which face each other, the container parts communicating with each other to form the container having a peripherally extending joint along which said container parts are sealed together and an outwardly directed flange adjacent the joint, one of the container parts being relatively stiff in comparison with the other and being provided with means defining an outlet opening, the other container part being more flexible to enable it to be pressed into said one container part and substantially into alignment with the inside thereof in order to empty the container; and the emptying device comprising: a holder for the container, the holder having means defining an opening therein and means defining a gap to position and receive most of the flange of the container, the opening defining means and the gap defining means being arranged in relation to each other so that when the flange is inserted in the gap defined by the gap defining means, the outlet opening defined in the container is in substantial alignment with the opening defined in the holder; said holder being provided with an integral emptying member located opposite the said opening defined therein and said emptying member and adjacent connecting portions of the holder being sufficiently flexible to be manually displaceable in the direction of said holder opening for emptying of the container upon displacement of the said emptying member a distance in the direction of the opening defined in the holder sufficient as to press in said other flexible container part until it substantially abuts the inside of said one container part secured to the holder.

2. A combination according to claim 1, wherein the emptying member comprises an end which, in use, will face the container, the end being rounded and having substantially the same dome shape as the interior of said one container part so as to be able to press said other container part into substantially complete contact with said one container part.

3. A combination according to claim 1, including a cannula secured releasably to said holder having an end thereof extending into said holder opening, the container having the shape of an ampoule and the outlet opening of the container being provided with a membrane, the opening defined in the holder being arranged to receive the cannula, said end of the cannula, when the cannula is secured to said holder, being located immediately opposite and spaced from said membrane and sufficiently close thereto so that the membrane can be punctured by the end of the cannula upon displacement of said emptying member.